United States Patent [19]

Heck et al.

[11] Patent Number: 4,898,853
[45] Date of Patent: Feb. 6, 1990

[54] ACETYLENIC ESTERS

[75] Inventors: James V. Heck, Scotch Plains; Michael D. Lewis, Rahway, both of N.J.

[73] Assignee: Merck & Co. Inc., Rahway, N.J.

[21] Appl. No.: 388,717

[22] Filed: Aug. 1, 1989

Related U.S. Application Data

[63] Continuation of Ser. No. 156,106, Feb. 16, 1988, abandoned.

[51] Int. Cl.$^4$ .................. A61K 31/695; C07F 7/18
[52] U.S. Cl. ...................... 514/63; 514/467; 514/549; 514/557; 514/567; 549/214; 549/215; 549/229; 556/419; 556/437; 556/438; 560/183; 562/555; 562/598
[58] Field of Search ............. 560/183; 514/549, 63; 556/438

[56] References Cited

U.S. PATENT DOCUMENTS

| | | | |
|---|---|---|---|
| 4,024,278 | 5/1977 | Henrick | 514/549 |
| 4,640,909 | 2/1987 | Ramsden et al. | 556/438 |
| 4,806,565 | 2/1989 | Hensens et al. | 549/229 |

FOREIGN PATENT DOCUMENTS

| | | | |
|---|---|---|---|
| 51-98225 | 1/1976 | Japan | 556/438 |
| 0174302 | 10/1983 | Japan | 514/549 |
| 0913903 | 12/1962 | United Kingdom | 560/183 |

OTHER PUBLICATIONS

M. D. Lewis & R. Menes, "Absolute and Relative Configuration of L-660, 631," Tetrahedron Lett., 43, 5129–5132 (1987).

R. M. Hanson & K. B. Sharpless, "Procedure for the Catalytic Asymmetric Epoxidation of Allylic Alcohols in the Presence of Molecular Sieves," J. Org. Chem., 51, 1922–1925 (1986).

M. Mehrabian et al., "Regulation of Rat Liver 3-Hydroxy-3-Methylglutaryl Coenzyme A Synthetase...," J. Biol. Chem. 261, 16249–16255 (1986).

M. Patel et al., Novel Antifungal Antibiotics, Sch 31828, Produced by Miccrobispora sp. SCC 1438, Abst. 983 of the 1987 Interscience Conference on Antimicrobial Agents & Chemotherapy.

*Primary Examiner*—Richard L. Raymond
*Attorney, Agent, or Firm*—Richard S. Parr; Michael C. Sudol

[57] ABSTRACT

This invention relates to acetylenic esters that are useful in the treatment of fungal diseases and hypercholesterolemic conditions.

11 Claims, No Drawings

ACETYLENIC ESTERS

This is a continuation of application Ser. No. 156,106 filed Feb. 16, 1988, now abandoned.

BACKGROUND OF THE INVENTION

This invention relates to acetylenic esters that are useful in the treatment of fungal diseases and hypercholesterolemic conditions.

Fermentation broths of certain strains of *Streptoverticillium hiroshimense* and Nocardia have been shown to produce the triyne carbonate 5-(1-hydroxy-2,4,6-heptatriynyl)-2-oxo-1,3-dioxolane-4-heptanoic acid, Formula A,

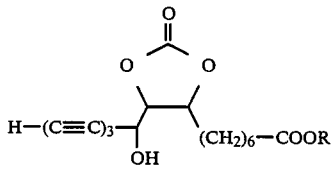

wherein R is hydrogen, or salts thereof. M. D. Lewis and R. Menes, *Tetrahedron Lett.*, 28, 5129–5132 (1987); See also U.S. patent application Ser. Nos. 07/053,920 (now U.S. Pat. No. 4,806,565), 07/053,921 (now U.S. Pat. No. 4,806,566), 07/053,926, and 07/053,973 (now U.S. Pat. No. 4,780,311), all filed May 26, 1987. The triyne carbonate A is a potent inhibitor of cytosolic β-ketothiolase, the initial enzyme of cholesterol biosynthesis, and is also active against certain fungal and bacterial strains. Utility against hypercholesterolemia and infectious diseases is limited, however, by the relative instability of the compound in vivo. The compounds of the present invention have been prepared as part of a program to improve both inherent biological activity and in vivo stability relative to the triyne carbonate of Formula A.

SUMMARY OF THE INVENTION

Applicants have discovered novel acetylenic esters of Formula I that are useful in the treatment of fungal diseases and hypercholesterolemic conditions.

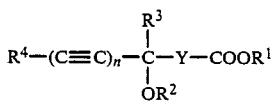

wherein $R^1$ is:
 (a) hydrogen;
 (b) $C_1$–$C_6$ alkyl;
 (c) $C_7$–$C_{14}$ aralkyl;
 (d) tris ($C_1$–$C_6$ alkyl)silyl; or
 (e) a pharmaceutically acceptable cation;
$R^2$ is:
 (a) hydrogen;
 (b) $C_1$–$C_6$ alkyl;
 (c) $C_7$–$C_{14}$ aralkyl;
 (d) tris ($C_1$–$C_6$ alkyl)silyl;
 (e) $C_2$–$C_6$ alkanoyl;
 (f) $C_2$–$C_7$ alkoxycarbonyl; or
 (g)

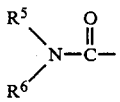

wherein $R^5$ and $R^6$ are independently:
 (i) hydrogen;
 (ii) $C_1$–$C_6$ alkyl; or
 (iii) phenyl;
$R^3$ is:
 (a) hydrogen; or
 (b) $C_1$–$C_6$ alkyl; or $R^2$ and $R^3$ taken together are a bond;
$R^4$ is:
 (a) hydrogen;
 (b) $C_1$–$C_6$ alkyl;
 (c) $C_7$–$C_{14}$ aralkyl; or
 (d) tris ($C_1$–$C_6$ alkyl)silyl;
Y is:
 (a) $C_4$–$C_{10}$ alkylene or $C_4$–$C_{10}$ alkylene substituted with one or more substituents selected from the group comprising:
  (i) hydroxy;
  (ii) $C_2$–$C_6$ alkanoyloxy; and
  (iii) $C_2$–$C_7$ alkoxycarbonyloxy; or
 (b)

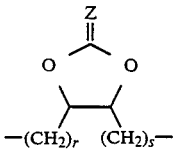

wherein Z is O or S, and r and s are independently integers of from about 0 to 8 such that the sum (r+s) is from about 2 to 8; and
n is an integer of from about 1 to 4, with the proviso that if n is 3, Y may not be

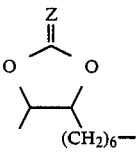

The term "$C_1$–$C_6$ alkyl" refers to straight or branched chain aliphatic hydrocarbons having from 1 to 6 carbon atoms and is also referred to as lower alkyl. Examples of $C_1$–$C_6$ alkyl are methyl, ethyl, propyl, butyl, pentyl, hexyl, and the isomeric forms thereof.

The term "$C_7$–$C_{14}$ aralkyl" refers to straight or branched chain alkyl groups bearing a phenyl or naphthyl group such that the total number of carbon atoms ranges from 7 to 14. Examples of $C_7$–$C_{14}$ aralkyl are benzyl, phenethyl, phenylpropyl, (1-naphthyl)methyl, (2-naphthyl)methyl, (1-naphthyl)ethyl, (2-naphthyl)ethyl, and the like, and isomeric forms thereof.

The term "tris($C_1$–$C_6$ alkyl)silyl" refers to a trisubstituted silyl group in which the $C_1$–$C_6$ alkyl groups may be the same or different. Examples of tris($C_1$–$C_6$ alkyl)silyl are trimethylsilyl, triethylsilyl, tert-butyldimethylsilyl, and the like.

The term "$C_2$–$C_6$ alkanoyl" refers to straight or branched chain alkanoyl groups having from 2 to 6 carbon atoms. Examples of $C_2$-$C_6$ alkyl are acetyl, propanoyl, butanoyl, pentanoyl, hexanoyl, and the isomeric forms thereof.

The term "$C_2$-$C_7$ alkoxycarbonyl" refers to straight or branched chain alkoxycarbonyl groups having from 2 to 7 carbon atoms. Examples of $C_2$-$C_7$ alkoxycarbonyl are methoxycarbonyl, ethoxycarbonyl, propoxycarbonyl, butoxycarbonyl, pentyloxycarbonyl, hexyloxycarbonyl, and the isomeric forms thereof.

The term "pharmaceutically acceptable cation" refers to a positively charged inorganic or organic ion that is generally considered suitable for human consumption. Examples of pharmaceutically acceptable cations are hydrogen, alkali metal (lithium, sodium, and potassium), magnesium ($\frac{1}{2}Mg^{++}$), calcium ($\frac{1}{2}Ca^{++}$), aluminum ($\frac{1}{3}Al^{+++}$), titanium ($\frac{1}{2}Ti^{++}$), zinc ($\frac{1}{2}Zn^{++}$), ammonium, alkylammonium, dialkylammonium, trialkylammonium, tetraalkylammonium, diethanolaminium, triethanolaminium, and guanidinium ions, and protonated forms of lysine, benzathine, procaine, chloroprocaine, choline, and meglumine. Cations may be exchanged by methods known in the art, such as ion exchange. Where compounds of Formula I are prepared in the carboxylic form, addition of a base form of the cation (such as a hydroxide or a free amine) will yield the appropriate cationic form.

The term "$C_4$-$C_{10}$ alkylene" refers to aliphatic hydrocarbon chains substituted at two different carbon atoms. Examples of $C_4$-$C_{10}$ alkylene are $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, and isomeric forms thereof.

The term "$C_2$-$C_6$ alkanoyloxy" refers to straight or branched chain alkanoyloxy groups having from 2 to 6 carbon atoms. Examples of $C_2$-$C_6$ alkyl are acetoxy, propanoyloxy, butanoyloxy, pentanoyloxy, hexanoyloxy, and the isomeric forms thereof.

The term "$C_2$-$C_7$ alkoxycarbonyloxy" refers to straight or branched chain alkoxycarbonyloxy groups having from 2 to 7 carbon atoms. Examples of $C_2$-$C_7$ alkoxycarbonyloxy are methoxycarbonyloxy, ethoxycarbonyloxy, propoxycarbonyloxy, butoxycarbonyloxy, pentyloxycarbonyloxy, hexyloxycarbonyloxy, and the isomeric forms thereof.

Compounds of Formula I in which $R^2$ and $R^3$ are taken together to form a bond are ketones. That is, the moiety $C(OR^2)(R^3)$ represents a carbonyl function, $C=O$.

It is to be recognized that certain compounds of Formula I possess one or more asymmetric carbon atoms and that certain compounds of this invention can exists as two or more optical isomers. Since these isomers may possess markedly different biological properties, it is advantageous to separate the enantiomers and use them in their pure form. The optically pure compounds of Formula I can be prepared from optically pure precursors. Alternatively, the compounds of Formula I can be resolved to their pure enantiomers by one or more methods known in the art. For example, compounds of Formula I in which $R^1$ is hydrogen or a corresponding pharmaceutically acceptable cation may be resolved by forming in a suitable solvent a salt of the racemic mixture with an optically active base such as (+)- or (−)-amphetamine, brucine, (+)-cinchonine, (−)-cinchonidine, strychine, (+)- or (−)-alpha-methylbenzylamine, (+)- or (−)-alpha-(1-naphthyl)ethylamine, and the like. Examples of suitable solvents include ethanol, isopropyl alcohol, benzene, acetonitrile, nitromethane, acetone, and the like. Two diasteromeric salts form in the solution, one salt usually being less soluble than the other. Repetitive recrystallization of the crystalline salt generally affords a pure diastereomeric salt from which is obtained the desired pure enantiomer, for example, by acidification of the salt with a mineral acid, filtration, and recrystallization.

The other optically pure antipode may generally be obtained by using a different optically active base to form the diastereomeric salt. It may be advantageous to isolate the partially resolved acid from the filtrates of the purification of the first diastereomeric salt, described above, and to purify further this substance through the use of another optically active base. It is especially advantageous for isolating the second enantiomer to use an optically active base that is the antipode of the base used for isolating the first enantiomer. For example, if (+)-alpha-methylbenzylamine was used first, the (−)-alpha-methylbenzylamine would be used to isolate the second (remaining) enantiomer.

DESCRIPTION OF THE INVENTION

The compounds of this invention can be prepared by methods illustrated in the following Schemes. Scheme A illustrates the preparation of alcohols of this invention of Formula IV (that is, Formula I wherein $R^2$ is hydrogen and A is $R^4$) and of derivatized alcohols of this invention of Formula X (that is, Formula I wherein $R^2$ is a group other than hydrogen and A is $R^4$).

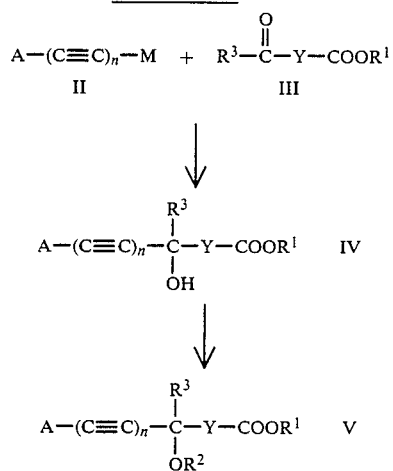

SCHEME A

Aldehydes or ketones of Formula III react with metallated acetylenes of Formula II, wherein A is $R^4$ or a suitable protecting group and M is a suitable metal or metal-containing species, to form alcohols of this invention of Formula IV. Although unprotected acetylenes (wherein A is hydrogen) are generally suitable for the reaction, protection of the acetylene terminus that is not intended to react provides greater control over formation and subsequent reactions of the metallated acetylenes. Suitable protecting groups are groups that mask the acetylene terminus, that do not react significantly to form by-products, and can readily be removed when protection is no longer desired. Preferred protecting groups include trialkylsilyl, preferably trimethylsilyl or t-butyldimethylsilyl, which can be attached using methods known in the art. For example, trialkylsilyl groups can be attached readily by exposing metallated acetylenes (derived from terminally unsubstituted acetylenes)

to trialkylsilylhalides. Metallated acetylenes are prepared from corresponding protected or unprotected acetylenes using methods known in the art, with the metal or metal-containing species M selected so as to allow the metallated acetylenes to react with the carbonyl group attached to $R^3$ without reacting significantly with other functionalities within compounds of Formula III. Suitable metals include alkali metals (preferably lithium) and alkaline earth metals (preferably magnesium). A preferred metallated acetylene species is a lithium acetylide formed in situ by the reaction of methyllithium with a silylated acetylene precursor of the formula $$A-(C{\equiv}C)_n-Si(Alkyl)_3$$

in a suitable organic solvent. The method is of particular use for preparing compounds of Formula I in which $R^4$ is a trialkylsilyl group. The metallated acetylene thus formed is then allowed to react with an aldehyde or ketone of Formula III to form an alcohol of Formula IV. Suitable organic solvents are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is an ether or cyclic ether such as diethyl ether or tetrahydrofuran. For compounds in which A is an acetylenic protecting group, removal of the protecting group provides alcohols of Formula IV wherein A is hydrogen (that is, Formula I of this invention wherein $R^2$ and $R^4$ are both hydrogen). The acetylenic protecting group can be removed using methods known in the art, such as solvolysis in an aqueous or alcoholic solvent system containing dilute acid or base or exposure to fluoride ion in a solvent containing a proton source. Preferred conditions for the removal of the acetylenic protecting group include treatment of the silylated acetylene with tetrabutylammonium fluoride and acetic acid in tetrahydrofuran.

Conversion of alcohols of Formula IV to derivatized alcohols of Formula V is effected by methods known in the art. For example, alkyl and aralkyl ethers can be formed by any of several alkylation methods known in the art. Silylated derivatives can be formed by reaction of the alcohol group with various silylating reagents, such as trialkylsilyl halides or hexaalkylsilazines, using methods well known in the art. Acylated derivatives can be formed by reaction with O-acylating reagents, such as acyl halides, acyl anhydrides, or isocyanates, using methods well known in the art. For compounds in which A is an acetylenic protecting group, removal of the protecting group, using methods as described above, provides derivatized alcohols of Formula V wherein A is hydrogen (that is, Formula I of this invention wherein $R^2$ is a group other than hydrogen and $R^4$ is hydrogen). Since certain of the substituents $R^2$ may be susceptible to removal under the conditions used for removal of the protecting group, the acetylenic protecting group may be removed before the alcohol group of compound IV is derivatized.

Scheme B illustrates the preparation of ketones of this invention of Formula VII (that is, Formula I wherein A is $R^4$ or a suitable protecting group and $R^2$ and $R^3$ together are a bond). Scheme B also illustrates an alternative method for preparing alcohols of Formula VIII (that is, Formula I wherein A is $R^4$ or a suitable protecting group and $R^2$ and $R^3$ are both hydrogen).

SCHEME B

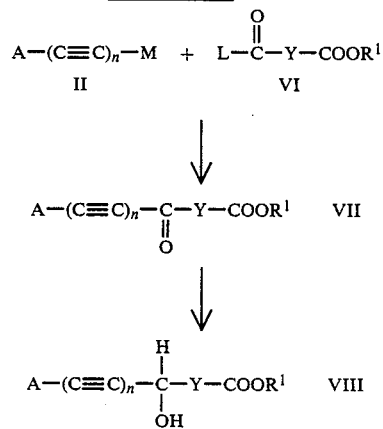

Activated acyl compounds of formula VI react with metallated acetylenes of Formula II, wherein A is $R^4$ or a suitable protecting group and M is a suitable metal or metal-containing species, to form ketones of this invention of Formula VII. Metallated acetylenes are prepared from corresponding protected or unprotected acetylenes using methods known in the art, with the metal or metal-containing species M selected so as to allow the metallated acetylenes to react with the activated acyl group without reacting significantly with other functionalities within compounds of Formula VI. For acyl halides of Formula VI (that is, wherein L is a halogen, preferably chlorine or bromine), preferred metals include transition metals, such as copper, and transition metal complexes, preferably copper-lithium combinations that can be preformed or prepared in situ. For mixing anhydrides of Formula VI (that is, wherein L is O-acyl), the preferred metallated acetylene species is an organolithium compound of the formula $$A-(C{\equiv}C)_n-Li$$

complexed with a Lewis acid (preferably boron trifluoride) in a suitable organic solvent. The metallated acetylene thus formed is then allowed to react with an activated acyl compound of Formula VI to form a ketone of Formula VII. Suitable organic solvents are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is an ether or cyclic ether such as diethyl ether or tetrahydrofuran. For compounds in which A is an acetylenic protecting group, removal of the protecting group as described above (see Scheme A) forms compounds of Formula VII wherein A is hydrogen (that is, Formula I wherein $R^2$ and $R^3$ together are a bond and $R^4$ is hydrogen).

Conversion of ketones of Formula VII to alcohols of Formula VIII can be effected using reduction methods well known in the art. For example, reduction can be effected using catalytic reduction or reaction with hydride reducing reagents such as modified alkali-metal aluminum hydrides or borohydrides. The alcohols VIII thus prepared can be derivatized using methods described above for Scheme A. As with compounds of Formula V, the acetylenic protecting group can be removed to form compounds of Formula VIII wherein A is hydrogen (that is, Formula I wherein $R^2$, $R^3$, and $R^4$ are each hydrogen).

Compounds of Formula III (see Scheme A) and Formula VI (see Scheme B) are readily available or can be prepared using methods known in the art. Where the alkylene group Y is substituted with hydroxy groups, reactions are best performed with suitable O-protecting groups known in the art. Where the alkylene group Y is substituted with alkanoyloxy or alkoxycarbonyloxy groups, the substituents need no further protection. Where not otherwise available, alkanoyloxy- or alkoxycarbonyloxy-substituted precursors of Formula III and VI can be prepared by acylating corresponding hydroxy-substituted compounds using methods well known in the art. Similarly, cyclic carbonate and cyclic thiocarbonate substitution can be obtained from corresponding vicinal diols by cyclization methods known in the art. Scheme C illustrates a method for preparing certain such cyclic carbonates of Formula XIII in which W is $R^3$ (that is, Formula III) or L (that is, Formula VI).

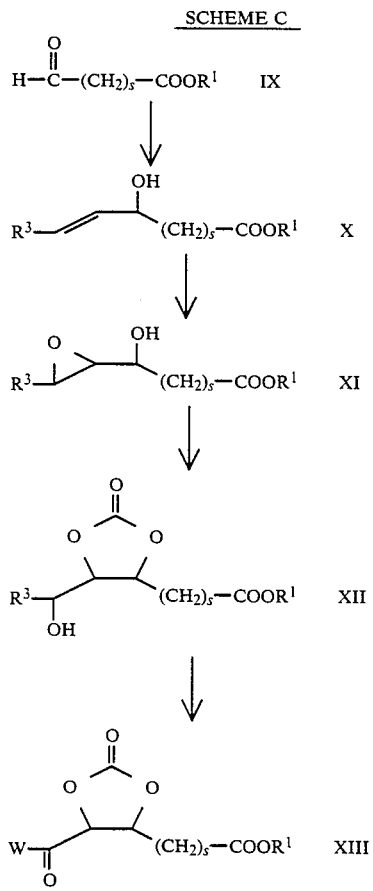

Aldehyde esters of Formula IX can be converted to allylic alcohols of Formula III by any of several methods known in the art. A preferred method employs a Grignard reaction. For example, reaction of aldehyde IX with a vinyl magnesium bromide of the formula $R^3$—CH=CH—MgBr in a suitable organic solvent (preferably tetrahydrofuran) at reduced temperatures (preferably about $-78°$ C.) affords the allylic alcohol X in good yields. Other suitable organic solvents are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art.

Allylic alcohols of Formula X are epoxidized by methods known in the art to form corresponding epoxy alcohols of Formula XI. A preferred epoxidation method employs a titanium(IV) salt (preferably titanium tetraisopropoxide) and an alkyl hydroperoxide (preferably t-butyl hydroperoxide) in a suitable solvent and is best performed in the presence of 3A molecular sieves. Suitable organic solvents for epoxidation are organic liquids in which the various reactants can be dissolved or suspended but which are otherwise chemically inert. Examples of suitable organic solvents include alkanes and cycloalkanes; aromatic hydrocarbons, such as benzene, toluene, and xylene; halocarbons, such as chloroform, dichloromethane, and ethylene dichloride; and other organic solvents known in the art. A preferred organic solvent is dichloromethane. Optically active epoxy alcohols of Formula IV can be prepared by the inclusion of an optically active induction agent such as L-(+)-diisopropyl tartrate (L-(+)-DIPT) or other such tartrate esters. For example, R. M. Hanson and K. B. Sharpless, *J. Org. Chem.*, 51, 1922–1925 (1986).

The alcohol function of a compound of Formula X is first acylated with a carbamate forming reagent using methods known in the art, and the resultant acylated intermediate is then ring closed to form the cyclic carbonate of Formula XII. Acylation is preferably performed using an aromatic isocyanate, preferably phenyl isocyanate, in a suitable organic solvent. An alternative acylation method uses a carbamoyl halide in a suitable organic solvent containing a suitable amine base. Suitable organic solvents for acylation are organic liquids in which the various reactants can be dissolved or suspended but which are otherwise chemically inert. Examples of suitable organic solvents include alkanes and cycloalkanes; alkanoate esters, such as ethyl acetate; ethers and cyclic ethers, such as diethyl ether, tetrahydrofuran, tetrahydropyran, and dioxane; aromatic hydrocarbons, such as dimethylformamide and N,N-dimethylacetamide; N-substituted lactams, such as N-methylpyrrolidinone and N-methylpiperidinone; halocarbons, such as chloroform, dichloromethane, and ethylene dichloride; cyanoalkanes, such as acetonitrile and propanenitrile; and other organic solvents known in the art. A preferred organic solvent is acetonitrile. Suitable amine bases are organic compounds that facilitate acylation and are sufficiently basic to prevent the reaction medium from becoming acidic but which do not themselves form significant quantities of by-products by reaction with other chemical reagents, intermediates, or reaction products. Suitable amine bases include tertiary amines and nitrogen-containing heteroaromatic compounds. Suitable tertiary amines include trialkylamines, such as triethylamine and tributylamine; N-substituted saturated heterocyclic compounds, such as N-methylmorpholine, N-methylpiperidine, and N,N-dimethylpiperazine; polybasic tertiary amines, such as N,N,N,N-tetramethylethylenediamine and N,N,N,N-tetramethylpropylenediamine; and other tertiary amines known in the art. Suitable nitrogen-containing heteroaromatic compounds include 1-methylpyrrole, pyridine, lutidine, pyrazine, pyrimidine, pyridazine, quinoline, isoquinoline, 1-methylimidazole, 1-methylpyrazole, dimethylaminopyridine, and other such nitrogen-containing heteroaromatic compounds known in the art. A preferred amine base is pyridine.

Ring closure of the acylated intermediate to compounds of Formula XII can be effected by any of several methods known in the art. A preferred ring closure method involves a Lewis-acid catalyzed reaction in a suitable organic solvent at reduced temperatures, preferably below at least about $-20°$ C. A preferred Lewis acid is boron trifluoride etherate. Suitable organic solvents for Lewis-acid catalyzed ring closure are organic liquids in which the various reactants can be dissolved or suspended but which are otherwise chemically inert. Examples of suitable organic solvents include alkanes and cycloalkanes; ethers and cyclic ethers, such as diethyl ether, tetrahydrofuran, tetrahydropyran, and dioxane; aromatic hydrocarbons, such as benzene, toluene, and xylene; and other organic solvents known in the art. A preferred organic solvent is diethyl ether. Analogous reactions using thiocarbamate forming reagents, such a phenyl isothiocyanate, instead of carbamate forming reagents yields thiocarbonate compounds analogous to carbonates of Formula XII, thereby providing access to compounds of Formula I wherein Z is S.

The alcohol group of a cyclic carbonate of Formula XII is then modified to form compounds of Formula XIII in which W is $R^3$ (that is, aldehydes or ketones; cf. Formula III, Scheme A) or a leaving group L (that is, activated acyl compounds; cf. Formula VI, Scheme B) for subsequent reactions. Conversion of compounds XII to aldehydes or ketones of formula XIII in which W is $R^3$ can be effected using any of several oxidation methods known in the art. For example, a preferred oxidation method employs a mixture of oxalyl chloride and dimethyl sulfoxide at reduced temperatures (preferably below at least $-35°$ C.) in a suitable organic solvent that is essentially inert under oxidative conditions, preferably tetrahydrofuran.

Conversion of compounds XII to activated acyl compounds of Formula XIII in which W is a leaving group L can be effected using methods known in the art. An alcohol of Formula XII is first oxidized to the corresponding carboxylic acid (that is, where W is OH) by any of several methods known in the art, and the resultant carboxylic acid is then converted to the desired activated acyl compound. A preferred method of oxidations uses Cr(VI) or permanganate under a variety of reaction conditions. For example, compounds of Formula XII can be oxidized in high yields using Jones oxidation with chromium trioxide in a mixture of sulfuric acid and acetone. Where the desired leaving group L is a halogen, preferably chlorine or bromine, the activated acyl compound of Formula XIII is an acid halide. Acid halides can be formed by a wide variety of methods using such reagents as oxalyl chloride, phosgene, phosphorus oxyhalides, thionyl halides, and the like. A preferred method for preparing acyl chlorides uses oxalyl chloride in a suitable organic solvent. Suitable organic solvents for preparing acyl halides are organic liquids in which the various reactants can be dissolved or suspended but which are otherwise chemically inert. Examples of suitable organic solvents for preparing acyl halides using oxalyl chloride include alkanes and cycloalkanes; alkanoate esters, such as ethyl acetate; ethers and cyclic ethers, such as diethyl ether, tetrahydrofuran, tetrahydropyran, and dioxane; aromatic hydrocarbons, such as benzene, toluene, and xylene; halocarbons, such as chloroform, dichloromethane, and ethylene dichloride; cyanoalkanes, such as acetonitrile and propanenitrile; and other organic solvents known in the art. A preferred organic solvent is dichloromethane.

Where the desired leaving group L is O-acyl, the activated acyl compound of Formula XIII is a mixed anhydride. Mixed anhydrides can be formed from the carboxylic acid intermediate by a wide variety of methods using such reagents as alkyl chlorocarbonates, preferably methyl chlorocarbonate or isobutyl chlorocarbonate, in a suitable organic solvent. The reaction can be performed in the presence of a suitable base or the carboxylic acid can first be converted to a salt. Suitable bases are chemical compounds that are sufficiently basic to prevent the reaction medium from becoming acidic but which do not themselves form significant quantities of by-products by reaction with other chemical regents, intermediates, or reaction products. Examples of suitable bases include tertiary amines, such as triethylamine, tributylamine, and N-methylmorpholine; hindered secondary amines, such as 2,2,6,6-tetramethylpiperdine; nitrogen-containing heteroaromatic species, such as pyridine, quinoline, and dimethylaminopyridine. A preferred base is a tertiary amine such as tributylamine. If salt formation is used instead, the carboxylic acid can be allowed to react with a base that does not release water or an alcohol as a by-product. Suitable bases for salt formation include alkali metal carbonates, such as lithium, sodium, and potassium carbonates; alkali metal hydrides, such as sodium and potassium hydrides; alkali metal alkyls, such as n-butyllithium and t-butyllithium; alkali metal salts of amines, such as lithium diisopropylamide and lithium hexamethyldisilazide; and other strong bases known in the art. A preferred base is n-butyllithium. By whichever means the mixed anhydride is formed, the organic solvent must be compatible with the basic conditions used. Suitable organic solvents include alkanes and cycloalkanes; ethers and cyclic ethers, such as diethyl ether, tetrahydrofuran, tetrahydropyran, and dioxane; aromatic hydrocarbons, such as dimethylforamide and N,N-dimethylacetamide; N-substituted lactams, such as N-methylpyrrolidinone and N-methylpiperidinone; cyanoalkanes, such as acetonitrile and propanenitrile; and other organic solvents known in the art. A preferred organic solvent is tetrahydrofuran.

The general methods described in Scheme C can be used to prepare unprotected vicinal diols intermediates (that is, where Y is alkylene substituted with two adjacent hydroxy groups). For example, using methods known in the art the expoxides can be ring opened or the cyclic carbonates can be hydrolyzed to corresponding triols. Selective protection of appropriate vicinal hydroxy groups using methods known in the art and subsequent oxidations of the unprotected hydroxy group as described in Schemes A and B would then yield the desired precursors of Formula III (see Scheme A) or Formula VI (see Scheme B).

The preferred embodiments of this invention include compounds of the following formula

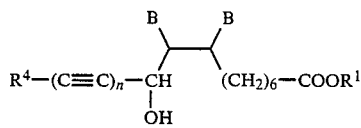

XIV wherein $R^1$ is hydrogen or methyl; wherein $R^4$ is hydrogen or trimethylsilyl; wherein B is hydrogen or hydroxy; and wherein n is 2 or 3.

More preferred embodiments of this invention include compounds of the following general formula

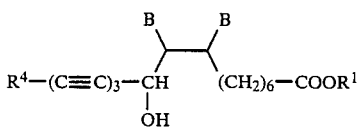

XV wherein $R^1$ is hydrogen or methyl; wherein $R^4$ is hydrogen or trimethylsilyl; and wherein B is hydrogen or hydroxy.

The compounds of this invention are useful in the treatment of fungal diseases and hypercholesterolemic conditions. Antihypercholesterolemic activity is illustrated by inhibition of acetoacetyl-coenzyme A thiolase, the enzyme involved in an early stage of cholesterol biosynthesis.

ACETOACETYL-COENZYME A THIOLASE INHIBITION

Acetoacetyl-coenzymne A thiolase was prepared from the livers of Sprague Dawley rats treated in the diet for one week with 0.075% lovastatin to induce the enzyme. Acetoacetyl-coenzyme A thiolase was purified through the DEAE-cellulose step essentially as described by Mehrabian et al., *J. Biol. Chem.*, 261, 16249–16255 (1986), but modified slightly by carrying out the 30–50% ammonium sulfate precipitation of the enzyme and a dialysis before the DEAE-cellulose step. The 0.06M eluate described by Mahrabian et al. contained the acetoacetyl-coenzyme A thiolase. The isolate was concentrated by ammonium sulfate precipitation, dissolved in the buffer used for elution, and stored at −70° C.

Inhibition of acetoacetyl-coenzyme A thiolase was measured by coupling the formation of acetoacetyl-coenzyme A to its subsequent reduction of β-hydroxybutyryl-coenzyme A dehydrogenase to β-hydroxybutyryl-coenzyme A and monitoring the resultant oxidation of NADH with a spectrophotometer set at 340 nm. Mixtures of 0.016 units of β-hydroxybutyryl-coenzyme A dehydrogenase, 16.2 μg of acetoacetyl-coenzyme A thiolase, and test quantities of the test compounds dissolved in dimethyl sulfoxide and water to bring to final volume were incubated with 71.4 mM Tris-HCl (pH 7.5), 0.71 mM EDTA, 10.7 mM magnesium chloride, 0.53 mM dithiothreitol, 0.21 mM NADH (total volume of 0.140 ml) until a stable base line was obtained. Reaction was initiated by addition of 10 μl of acetoacetyl-coenzyme A, giving a concentration of 2.85 mM. Reaction was measured at room temperature for a time period necessary to produce a measurable reaction rate. An $IC_{50}$, the concentration that inhibits 50% of the acetoacetyl-coenzyme A thiolase activity, was determined for each test compound. The $IC_{50}$'s for representative compounds of this invention are listed in Table I. The $IC_{50}$ of 5-(1-hydroxy-2,4,6-heptatriynyl)-2-oxo-1,3-dioxolane-4-heptanoic acid has been reported as $1 \times 10^{-8}$M. See U.S. patent application Ser. No. 07/053,973, filed May 26, 1987.

TABLE 1
Inhibition of Acetoacetyl-coenzyme A Thiolase

| Compound (Example No.) | $IC_{50}$ (μM) |
|---|---|
| Ex. 1 | 0.15 |
| Ex. 2 | 38 |
| Ex. 3 | 0.017 |
| Ex. 4 | 0.024 |
| Ex. 5 | >62 |
| Ex. 6 | 26 |

By virtue of their antifungal and antihypercholesterolemic activities, the compounds of Formula I are useful in treating fungal diseases and hypercholesterolemia in mammals. A physician or veterinarian or ordinary skill can readily determine whether a subject exhibits the conditions. Regardless of the route of administration selected, the compounds of the present invention can be formulated into pharmaceutically acceptable dosage forms by conventional methods known to those skilled in the art. The non-ester compounds of this invention may also be formulated as pharmaceutically acceptable base addition salts. Moreover, the compounds or their salts may be used in a suitable hydrated form.

The compounds of this invention may be used in any of a variety of pharmaceutical preparations. The compounds can be administered orally in such oral dosage forms as tablets, capsules, pills, powders, granules, elixirs, or syrups. The compounds may be administered by injection intravascularly, intraperitoneally, subcutaneously, or intramuscularly using forms known to the pharmaceutical art. The compounds may also be administered topically using forms known to the pharmaceutical art. In general, the preferred form of administration is by injection.

For the orally administered pharmaceutical compositions and methods of the present invention, a therapeutically effective amount of the foregoing active ingredients will typically be administered in admixture with suitable pharmaceutical diluents, excipients, or carriers (collectively referred to herein as "carrier" materials) suitably selected with respect to the intended form of administration (that is, oral tablets, capsules, pills, powders, granules, elixirs, syrups, and the like) and consistent with conventional pharmaceutical practice. For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, and combinations thereof. Lubricants for use in these dosage forms include boric acid, sodium benzoate, sodium acetate, sodium chloride, and the like, or combinations thereof. Disintegrators include without limitation starch, methylcellulose, agar, bentonite, guar gum, and the like, or combinations thereof. Sweetening agents and preservatives can also be included where appropriate.

For the injectable pharmaceutical compositions and methods of the present invention, a therapeutically effective amount of the foregoing active ingredients will typically be administered in such forms as solutions, suspensions, or emulsions in oily or aqueous carriers. Suitable carriers include water, saline, aqueous dextrose, polyethylene glycol, various buffers, and the like. The injectable pharmaceutical compositions may include various formulatory agents known in the art. The injectable pharmaceutical compositions may be prepared in unit dosage form or in multidose containers or may be prepared in powdered form for reconstitution at the time of delivery with a suitable carrier, such as sterile water.

For the topically applied pharmaceutical compositions of the present invention, a therapeutically effective amount of the foregoing active ingredients will typically be formulated in hydrophobic or hydrophilic bases as ointments, creams, lotions, paints, or powders.

By whatever route of administration selected, a therapeutically effective but non-toxic amount of the compound is employed in treatment. The dosage regimen for preventing or treating fungal diseases or hypercholesterolemia with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until an optimal response is obtained. Doses for injection are ordinarily in the range of about 1 mg/kg up to about 50 mg/kg, preferably in the range of about 10 mg/kg.

The following examples further illustrate details for the preparation of the compounds of this invention. The invention, which is set forth in the foregoing disclosure, is not to be constructed or limited either in spirit or in scope by these examples. Those skilled in the art will readily understand that known variations of the conditions and processes of the following preparative procedures can be used to prepare these compounds. All temperatures are degrees Celsuis unless otherwise noted.

DESCRIPTION OF THE PREFERRED EMBODIMENTS

EXAMPLE 1

8(S),9(S),10(R)-Trihydroxy-11,13,15-hexadecatriynoic acid

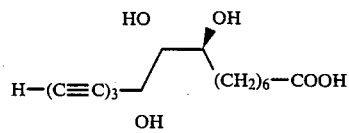

5-(1(R)-Hydroxy-2,4,6-octatriynyl)-2-oxo-4(S),5(S)-1,3-dioxolane-4-heptanoic acid (see, for example, Lewis and Menes, "Tetrahedron Lett., 28, 5129–5132 (1987)) was dissolved in diethyl ether and washed several times with a pH 10 buffer. The combined buffer layers were left standing for one hour, then were cooled with an ice bath and acidified to pH 2. Extraction with several volumes of ethyl acetate and partial concentration in vacuo afforded a solution of the title compound (approximately 1 mg/ml) in ethyl acetate. Structure assignment of the subsequently prepared methyl ester (see Example 2) was supported by nmr spectroscopy.

EXAMPLE 2

8(S),9(S),10(R)-Trihydroxy-11,13,15-hexadecatriynoic acid, methyl ester

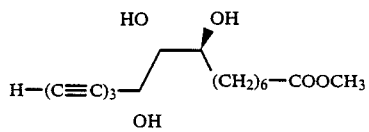

A quantity of a 1 mg/ml solution in ethyl acetate of 8(S),9(S),10(R)-trihydroxy-11,13,15-hexadecatriynoic acid (10 ml, 34.2 μmols) was stirred at ambient temperature in a flask equipped with a vacuum adapter. A solution of $CH_2N_2$ in diethyl ether (1 ml) was added and the progress of the reaction followed by thin layer chromatography. After 10 minutes, vacuum was applied and the excess $CH_2N_2$ was removed. The mixture was partially concentrated to 0.2 ml and applied to a short silica gel column. The desired material was eluted with diethyl ether. After partial concentration, the solvent was replaced by repeated removal of $CDCl_3$ under reduced pressure and the reaction quantized by nmr spectroscopy (using an internal standard) to establish recovery of the title compound (6.8 mg, 65%). Structure assignment was supported by the nmr spectrum.

$^1$NMR (300 MHz, $CDCl_3$):
δ (ppm) 2.14 (1H, s); 2.330 (2H, d, J=7.4 Hz); 3.685 (3H, s); 4.7 (3H, m).

EXAMPLE 3

10-Hydroxy-16-(trimethylsilyl)-11,13,15-hexadecatriynoic acid, methyl ester

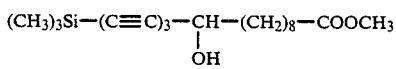

To bis-1,6-trimethylsilylhexa-1,3,5-triyne (21.35 mg, 97.8 μmols) stirred at −78° C. in dry tetrahydrofuran (THF) (1.0 ml) under argon was added methyl lithium in diethyl ether (69.8 μl, 97.8 μmols) and the mixture stirred 15 minutes. After being warmed to 0° C., the mixture was stirred for an additional hour. The solution was then recooled to −78° C. and methyl 8-oxodecanoate (20.1 μl, 97.8 μmols) was added dropwise. The resulting mixture was stirred for thirty minutes and then quenched with saturated NH₄Cl (1.0 ml), and allowed to warm to ambient temperature. After dilution with diethyl ether, the mixture was washed twice with water and once with brine, then dried with MgSO₄ and filtered. Concentration at reduced pressure afforded a light brown oil (27.3 mg).

Purification by silica gel preparative layer chromatography (eluting with 20% diethyl ether:hexanes) furnished the title compound (7.2 mg, 21%) as a clear oil. Structure assignment was supported by nmr spectroscopy.

$^1$H NMR (300 MHz, CDCl₃):

δ (ppm) 0.207 (9H, s); 2.307 (2H, d, J=7.5 Hz); 3.671 (3H,s); 4.430 (1H, q, J=6.3 Hz).

EXAMPLE 4

10-Hydroxy:11,13,15-hexadecatriynoic acid, methyl ester

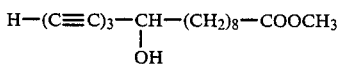

Other eluate fractions from the chromatography described in Example 3 furnished the title compound (5.4 mg, 20%) as a clear oil. Structure assignment was supported by nmr spectroscopy.

$^1$H NMR (300 MHz, CDCl₃):

δ (ppm) 2.150 (1H, s); 2.307 (2H, d, J=7.5Hz); 3.670 (3H, s); 4.429 (1H, q, J=6.3 Hz).

EXAMPLE 5

10-Hydroxy-14-(trimethylsilyl)-11,13-tetradecadiynoic acid, methyl ester

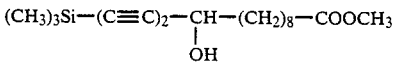

The title compound (31.5 mg, 51%) was prepared by the method of Example 3 using the appropriate lithiated diyne. Purification by silica gel preparative layer chromatography (eluting with 5% diethyl ether:hexanes) furnished the title compound as a clear oil. Structure assignment was supported by nmr spectroscopy.

$^1$H NMR (300 MHz, CDCl₃):

δ (ppm) 0.193 (9H, s); 1.830 (1H, d, J=5.6 Hz); 2.300 (2H, d, J=7.5 Hz); 3.664 (3H, s); 4.408 (1H, q, J=6.3 Hz).

EXAMPLE 6

10-Hydroxy-11,13-tetradecadiynoic acid, methyl ester

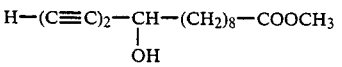

Other eluate fractions from the chromatography described in Example 5 furnished the title compound (6.2 mg, 13%) as a clear oil. Structure assignment was supported by nmr spectroscopy.

$^1$H NMR (300 MHz, CDCl₃):

δ (ppm) 1.842 (1H, d, J=5.7 Hz); 2.199 (1H, d, J=1.1. Hz); 2.307 (2H, d, J=7.5 Hz); 3.670 (3H, s); 4.412 (1H, q, J=6.2 Hz).

What is claimed is:

1. A compound of the formula:

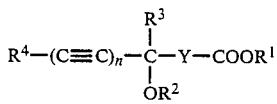

wherein R¹ is:
(a) hydrogen:
(b) C₁–C₆ alkyl;
(c) C₇–C₁₄ aralkyl;
(d) tris (C₁–C₆ alkyl)silyl; or
(e) a pharmaceutically acceptable cation;

R² is:
(a) hydrogen;
(b) C₁–C₆ alkyl;
(c) C₇–C₁₄ aralkyl ;
(d) tris (C₁–C₆ alkyl)silyl;
(e) C₂–C₆ alkanoyl;
(f) C₂–C₇ alkoxycarbonyl; or R³ is:
(a) hydrogen; or
(b) C₁–C₆ alkyl;

R⁴ is
tris(C₁–C₆ alkyl)silyl;

Y is:
C₄–C₁₀ alkylene or C₄–C₁₀ alkylene substituted with one or more substituents selected from the group comprising:
(i) hydroxy;
(ii) C₂–C₆ alkanoyloxy; and
(iii) C₂–C₇ alkoxycarbonyloxy; and n is an integer of from about 1 to 4.

2. A compound according to claim 1 having the formula:

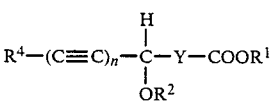

wherein R¹ is:
(a) hydrogen;
(b) C₁–C₆ alkyl; or
(c) a pharmaceutically acceptable cation;

R² is:
(a) hydrogen;
(b) C₁–C₆ alkyl;
(c) C₇–C₁₄ aralkyl;
(d) tris(C₁–C₆ alkyl)silyl;
(e) C₂–C₆ alkanoyl;
(f) C₂–C₇ alkoxycarbonyl;

R⁴ is
tris(C₁–C₆ alkyl)silyl;

Y is C₄–C₁₀ alkylene or C₄–C₁₀ alkylene substituted with one or more hydroxy; and n is an integer of from about 1 to 3.

3. A compound according to claim 2 having the formula:

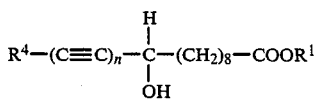

wherein $R^1$ is:
 (a) hydrogen;
 (b) $C_1$–$C_6$ alkyl; or
 (c) a pharmaceutical acceptable cation;
$R^4$ is
 tris($C_1$–$C_6$ alkyl)silyl; and
n is an integer of from about 1 to 3.

4. A compound according to claim 3 wherein n is 3.

5. A compound according to claim 4 which is 10-hydroxy-16-(trimethylsilyl)-11,13,15-hexadecatriynoic acid, methyl ester.

6. A compound according to claim 3 wherein n is 2.

7. A compound according to claim 6 which is 10-hydroxy-14-(trimethylsilyl)-11,13-tetradecadiynoic acid, methyl ester.

8. A compound according to claim 2 having the formula:

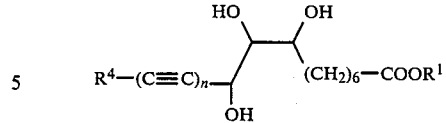

wherein $R^1$ is:
 (a) hydrogen;
 (b) $C_1$–$C_6$ alkyl; or
 (c) a pharmaceutically acceptable cation;
$R^4$ is
 tris($C_1$–$C_6$ alkyl)silyl; and
n is an integer of from about 1 to 3.

9. A compound according to claim 7 wherein n is 3.

10. A pharmaceutical composition useful in the treatment of fungal diseases ar hypercholesterolimic conditions comprising a therapeutically effective amount of at least one compound according to claim 1, together with one or more non-toxic pharmaceutically acceptable carriers.

11. A pharmaceutical composition according to claim 14 wherein said compound is selected from the group consisting of:
 10-hydroxy-16-(trimethylsilyl)-11,13,15-hexadecatriynoic acid, methyl ester and
 10-hydroxy-14-(trimethylsilyl)-11,13-tetradecadiynoic acid, methyl ester.

* * * * *